United States Patent [19]

Hayasaka et al.

[11] Patent Number: 5,510,327
[45] Date of Patent: Apr. 23, 1996

[54] HIGHLY CONCENTRATED TCF PHARMACEUTICAL PREPARATIONS

[75] Inventors: Hitoshi Hayasaka, Ohaza-ishibashi; Nobuyuki Kawashima, Ishibashimachi; Masatsugu Ueda, Kawagoe; Eitaro Kumazawa, Ohaza-yakushiji, all of Japan

[73] Assignee: Snow Brand Milk Products Co., Ltd., Hokkaido, Japan

[21] Appl. No.: 198,893

[22] Filed: Feb. 18, 1994

[30] Foreign Application Priority Data

Feb. 23, 1993 [JP] Japan .................. 5-057826

[51] Int. Cl.⁶ .................. A61K 38/17
[52] U.S. Cl. .................. 514/8; 514/21; 514/970
[58] Field of Search .................. 514/8, 21, 970; 530/395

[56] References Cited

U.S. PATENT DOCUMENTS

| | | | |
|---|---|---|---|
| 4,076,701 | 2/1978 | Burton et al. | 260/112 B |
| 4,481,137 | 11/1984 | Ohnishi et al. | 260/112 R |
| 4,650,674 | 3/1987 | Aggarwal et al. | 424/85 |
| 4,777,241 | 10/1988 | Irikura et al. | 530/350 |
| 4,822,605 | 4/1989 | Powell | 424/85.2 |
| 4,870,163 | 9/1989 | Rubin et al. | 530/413 |
| 5,328,836 | 7/1994 | Shima et al. | 435/69.4 |

FOREIGN PATENT DOCUMENTS

| | | |
|---|---|---|
| 0456188A1 | 11/1991 | European Pat. Off. . |
| 0462277A1 | 12/1991 | European Pat. Off. . |
| 0462549A1 | 12/1991 | European Pat. Off. . |

OTHER PUBLICATIONS

K. Michael Weidner et al., "Evidence for the Identify of Human Scatter Factor and Human Hepatocyte Growth Factor", *Proc. Natl. Acad. Sci. USA*, 88:7001–7005 (1991).

*Primary Examiner*—S. Mark Clardy
*Attorney, Agent, or Firm*—Testa, Hurwitz & Thibeault

[57] ABSTRACT

This invention provides pharmaceutical preparations containing highly concentrated tumor cytotoxic factor (TCF). The pharmaceutical preparations of the present invention contain highly concentrated TCF and a basic amino acid or their salts, or an organic or inorganic salt as a solubizer. The resultant compositions described in the present invention dissolve TCF at high concentrations of 10 mg/ml or over under about neutral and isotonic conditions. The resultant compositions are stable and are suitable for injection preparations.

17 Claims, 3 Drawing Sheets

---: 5 °C
———: 20 °C
○ : 0.15 M NaCl, pH 7.0
◇ : 0.3 M NaCl, pH 7.0
● : 0.15 M NaCl, pH 6.0

---: 5 °C
—: 20 °C
○ : 0.5 % HSA
  0.15 M NaCl
  0 % D-mannitol, pH 7.0
◇ : 0.5 % HSA
  0.075 M NaCl
  2.5 % D-mannitol, pH 7.0
● : 0.5 % HSA
  0.15 M NaCl
  0 % D-mannitol, pH 6.0
◆ : 0.5 % HSA
  0.075 M NaCl
  2.5 % D-mannitol, pH 6.0

HIGHLY CONCENTRATED TCF PHARMACEUTICAL PREPARATIONS

FIELD OF THE INVENTION

This invention relates to pharmaceutical preparations having tumor cytotoxic factor activity.

BACKGROUND OF THE INVENTION

Tumor cytotoxic factor, hereinafter abbreviated as TCF, is an another name of TCF-II found in a cultured supernatant of human fibroblast cells and disclosed in WO 90/10651. TCF is a glycoprotein consisting of heterodimer having molecular weight of about 76–80 kDa in unreduced state, and α subunit having molecular weight of about 52–56 kDa and β or β' subunit having molecular weight of about 30–36 kDa in reduced state.

TCF exhibits various biological activities such as the activities of hepatocyte growth factor; HCF, scatter factor; SF, proliferation factor of renal tubular epithelial cells, repair factor for damaged tissues and proliferation factor of vascular endothelial cells. In addition to TCF activity. TCF is a cytokine belonging to a member of HCF family. TCF is expected to be developed as pharmaceuticals for the treatment of diseases of liver and kidneys, wounds and tumors due to its various kinds of physiological activity.

However, the solubility in water of TCF is very low. Thus aqueous preparations such as injections with high concentrations satisfying medical use are hardly obtained. Therefore, one of the most serious subject to be solved for its application to the clinical use is preparing such a concentrated solution of TCF. TCF has rapid metabolic turnover in vivo and high dosage is expected on the clinical use. The clinical dosage of TCF is expected to be 1 10 mg/day for adult patients. To make sure of the quality of final products, such as injections, the production processes require to dissolve TCF at high concentrations and to mix it with additives such as stabilizers under low temperatures. Furthermore, a highly concentrated TCF solution is demanded for medical treatment, that is the solution of neutral pH and has isotonicity for injections. No such method to prepare highly concentrated TCF solution has been developed yet. For example, an isotonic saline solution, containing 0.15M sodium chloride usually used for injections, dissolves TCF less than 5 mg/ml and the TCF solution is unstable. The solubility of TCF decreases and TCF becomes insoluble with the progress of time at room temperature. Furthermore, solubility of TCF in saline markedly decreases to about 1 mg/ml at 5° C. or lower.

Therefore, it is an important subject to establish a method for preparing a neutral, isotonic and highly concentrated TCF solution at low temperatures. Above mentioned WO 90/10651 discloses preparations containing a protein, a sugar, an amino acid and so forth as an adsorption preventive agent or a stabilizer. However, neither highly concentrated TCF solution of the present invention is disclosed nor suggested.

Thus, the object of the present invention is to provide a highly concentrated and isotonic TCF injection solutions for medical treatment.

SUMMARY OF THE INVENTION

Figure 1:
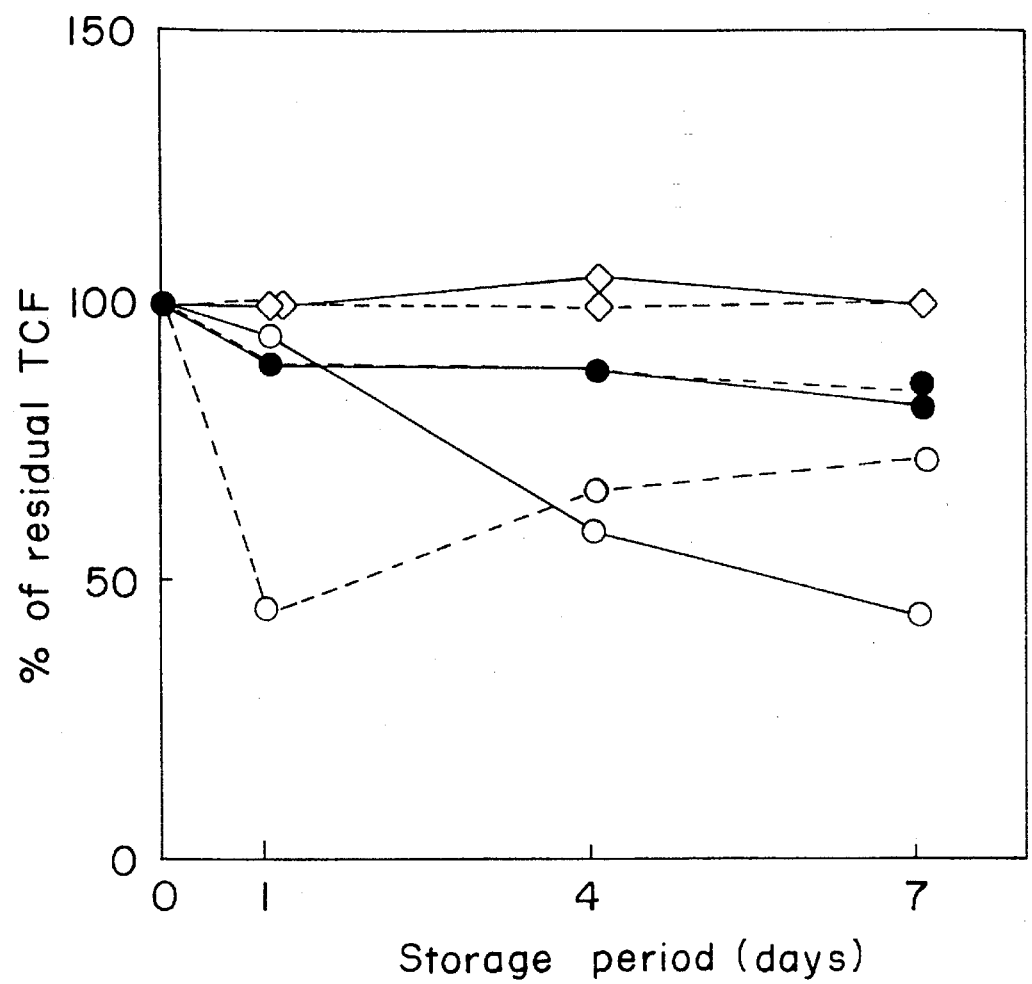
FIG. 1 shows a stability on storage of the TCF solution prepared by adding sodium chloride as an dissolution adjubant.

The inventors have been investigating to overcome the difficulty in dissolving TCF at high concentrations and found the following characteristic feature of solubility of TCF and accomplished the present invention.

(1) TCF shows temperature dependent solubility in water.

(2) TCF exhibits higher solubility at lower pH regions under a pH range of 5–8.

(3) Addition of a salt such as sodium chloride, preferably at concentrations of 0.3M or over, provides markedly increased solubility of TCF.

(4) Addition of a basic amino acid, preferably 1.0–4.0% of arginine or lysine, markedly elevates the solubility under neutral pH and isotonicity of about 300 mOsm.

One object of the present invention is to provide preparations of TCF solution with improved solubility to satisfy the use for medical treatments.

Other object of the present invention is to provide highly concentrated TCF solution containing one or more solubilizing agents selected from the group consisting of basic amino acids or their salts, and these amino acids together with pharmacologically acceptable organic or inorganic salts.

Further object of the present invention is to provide highly concentrated TCF injections with neutral pH and isotonicity containig one or more solubilizing agents selected from the group consisting of basic amino acids or their salts, and these amino acids together with pharmacologically acceptable organic or inorganic salts.

DETAILED DESCRIPTION OF THE INVENTION

The TCF pharmaceuticals of the present invention contain 5 mg/ml or over TCF together with a basic amino acid and/or inorganic or organic salt as solubilizing agent(s) at concentrations to give isotonic solution. The pharmaceuticals of the present invention must be homogenous mixtures of TCF and the solubilizing agent(s) in the case of dissolving them before use. To prepare these pharmaceuticals, the TCF solution at the desired concentration must be prepared and divided in vials or ampoules, optionally lyophilyzed, and sealed. Highly concentrated TCF solutions are essential to prepare these pharmaceuticals. However, the solubility of TCF in water is very low. Acidic condition of pH 6 or less, or ionic strength of 0.3M or over of sodium chloride is required to increase the solubility of TCF. But acidic injections cause patients pain on injection and are undesirable. Also, a higher concentration of sodium chloride is undesirable because of raising osmotic pressure of the injections.

To maintain isotonicity, one may prepare 0.15M sodium chloride solution having osmotic pressure of about 300 mOsm. However, this solution dissolves only about 1 mg/ml of TCF at low temperature. To dissolve TCF up to about 10 mg/ml, 0.3M or over sodium chloride solution is required, but its osmotic pressure becomes 600 mOsm or over. Therefore, multiple solubilizing agents are required to obtain the solution dissolving TCF at 10 mg/ml or over on the isotonic condition.

As solubilizing agents, basic amino acids and organic or inorganic salts and both of them can be used. Arginine or lysine is preferable as a basic amino acid and their salts also be used. Solutions containing these amino acids or their salts at concentrations of 3–4% of as free amino acid are almost isotonic. These solutions can dissolve TCF at concentrations of 10–20 mg/ml. Furthermore, these basic amino acids or their salts may be combined with one or more organic and inorganic salts. For examples, 1.5–1.75% of the amino acid solution with pharmacologically acceptable organic and inorganic salts can be isotonic. Sodium citrate or sodium lactate may be exemplified as organic salts. Sodium chloride, disodium hydrogenphosphate or sodium hydrogencarbonate may be exemplified as inorganic salts, and sodium chloride is preferable. TCF dissolves at concentration of 5–10 mg/ml by using the basic amino acid with the salt. This TCF solution can be used as injections after being sterilized, divided in vials or ampoules and sealed. Also the solution may be freeze-dried to give lyophilized pharmaceuticals. Lyophilized pharmaceuticals may be prepared by dissolving TCF at twofold concentration into a solution containing a basic amino acid and a salt at two times concentration (e.g. 7% or higher basic amino acid or a combination of 4% of basic amino acid and 0.15M sodium chloride) and lyophilizing, as TCF easily dissolves at a high concentration in a solution of a basic amino acid and a salt. This procedure may reduce time and energy required for lyophilization. The lyophilized preparations may be re-dissoleved in twofold distilled water for injection to give isotonic intramuscular or intravenous injections. The TCF pharmaceuticals or injections of the present invention include these lyophilized pharmaceuticals.

As TCF is easily adsorbed to glass or synthetic resins, addition of a surfactant, an adsorption preventive agent or a stabilizer may be helpful to prevent TCF from adsorping. Tween 20, Tween 80 and Tween 100 can be exemplified as surfactat. Human serum albumin, gelatin, sorbitol, mannitol and xylitol disclosed in WO 90/10651 may be exemplified as adsorption preventive agents and stabilizers.

The TCF pharmaceutical preparations of the present invention can be stored for a long period of time maintaining sufficient amount of TCF for the treatment of diseases which require highly concentrated solution of TCF.

The present invention will be explained by the following examples and reference examples. The present invention, however, is not restricted by these examples.

EXAMPLES

The present examples show the preparation of highly concentrated pharmaceuticals of TCF.

TCF used for examples, reference examples and experiments is recombinant TCF (r-TCF) produced by genetically engineered Namalwa cells by application of recombinant DNA technique according to the method disclosed in WO 92/1053. Solutions containing TCF were prepared with 10 mM phosphate buffer containing 0.01% Tween 80 as an adsorption preventive agent.

(1) A preparation of injections containing TCF at high concentration

① TCF solution was prepared by dissolving TCF to 20 mg/ml in an aseptic pyrogen-free 10 mM phosphate buffer (pH 7) containing 0.01% of Tween 80 and 0.3M of sodium chloride.

② An aseptic pyrogen-free 10 mM phosphate buffer (pH 7) containing 2.33% L-arginine hydrochloride and 0.01% Tween 80 was prepared. This solution and the TCF solution prepared in ① were mixed at a ratio of 3:1. After the solutions were mixed well, the mixed solution was sterilized with a filter having 0.22 μm pores and divided 1 ml each in ampoules and sealed. The prepared solution showed neutral pH and isotonicity and contained 5 mg/ml of TCF, 0.075M of sodium chloride and 1.75% L-arginine hydrochloride. Therefore this solution is most preferably for injections as pharmaceuticals. Furthermore, the solution is stable without becoming turbid and maintains the initial concentration of TCF at room temperature or lower.

(2) A preparation of injections containing TCF at high concentration

TCF was dissolved to 10 mg/ml in an aseptic pyrogen free 10 mM phosphate buffer (pH 7) containing 3.5% of DL-arginine hydrochloride and 0.01% of Tween 80. This TCF solution was sterilized with the filter and divided 1 ml each to vials and sealed. The solution, showed neutral pH and isotonicity and contained 10 mg/ml of TCF, is most preferable for injections. Furthermore, the solution is stable without becoming turbid and maintains the initial concentration of TCF at room temperature or lower.

(3) A preparation of injections containing TCF at high concentration

TCF was dissolved to 10 mg/ml in an aseptic pyrogen-free 10 mM phosphate buffer (pH 7) containing 3.0% of L-lysine hydrochloride and 0.01% of Tween 80. This TCF solution was sterilized with the filter and divided 1 ml each to vials and sealed. The solution, shows neutral pH and isotonicity and contains 10 mg/ml of TCF, is most preferable for injections. Furthermore, the solution is stable without becoming turbid and maintains the initial concentration of TCF at room temperature or lower.

(4) A Preparation of Lyophilized Injections Containing TCF at High Concentration TCF was dissolved to 10 mg/ml in an aseptic pyrogen-free 10 mM phosphate buffer (pH 7) containing 7.0% of DL-arginine hydrochloride and 0.02% of Tween 80. This TCF solution was sterilized with the filter, divided 1 ml each to vials, lyophilized and sealed. The lyophilized preparation was re-dissolved in 2 ml of distilled water for injection before use to give 5 mg/ml solution of TCF which showed neutral pH and isotonicity.

EXPERIMENT 1

The solubility test of TCF is explained by the following test experiments. The present test gave findings concerning the profile of TCF solubility required for preparaing pharmaceuticals of TCF.

(1) Evaluation of Solubility of TCF

TCF was weighed in polypropylene tubes, and solutions of various pHs containing various concentrations of sodium chloride and/or an amino acid were added into the tubes. To dissolve TCF, the tubes were immediately placed at a constant temperature and stirred for 30 min. according to the method described in the XIIth Pharmacopoeia of Japan (JP XII), General notices 24. The tubes were ultracentrifuged at 30,000×g for 30 min. at a constant temperature to separate unsolved TCF. The concentration of TCF in the obtained saturated TCF solutions was measured by Lowry-Folin's method to determine solubility of TCF.

(2) Effect of pH on Solubility of TCF

Solutions of various pHs containing 0.15M sodium chloride or not were prepared. Solubilities of TCF in these solutions were determined at 5° C. and 20° C. according to the method shown in experiment (1) and the results are shown in Table 1. The results showed that the solubilities of TCF were increased depending on the decline of pH at pH 7 or lower.

TABLE 1

| pH | 0 M NaCl 20° C. | 0.15 M NaCl 5° C. | 0.15 M NaCl 20° C. |
|---|---|---|---|
| 5.5 | 1.9 | 5.6 | 15.0 |
| 6.0 | 1.0 | 2.8 | 12.4 |
| 6.5 | 0.6 | 1.7 | 6.5 |
| 7.0 | 0.4 | 1.2 | 4.9 |
| 7.5 | — | — | 4.6 |
| 8.0 | — | — | 4.8 |

*Solubility is expressed as mg/ml.

(3) Effect of Concentration of Sodium Chloride on Solubility of TCF

Solutions of various concentration of sodium chloride at pH 6, pH 0.5 and pH 7 were prepared. Solubilities of TCF in these solutions were determined at 20° C. according to the method shown in experiment (1) and the results are shown in Table 2. The results showed the remarkable increase of solubility of TCF when the concentration of sodium chloride was raised from 0.15M to 0.3M. However, the increase of concentration of sodium chloride from 0.3M to 1.2M made a slight raise of the solubility of TCF.

TABLE 2

| Concentration of sodium chloride (M) | pH 6.0 | pH 6.5 | pH 7.0 |
|---|---|---|---|
| 0 | 1.0 | 0.6 | 0.4 |
| 0.15 | 12.4 | 0.5 | 4.0 |
| 0.3 | 53.7 | 51.4 | 40.4 |
| 1.2 | 62.1 | 57.5 | 53.9 |

*Solubility is expressed as mg/ml.

(4) Effect of Temperature on Solubility of TCF

Solutions containing 0.15M or 0.3M sodium chloride at pH 6, pH 6.5 and pH 7 were prepared. Solubilities of TCF in these solutions were determined at different temperatures according to the method shown in experiment (1) and the results are shown in Table 3. The results showed the remarkable increase of solubility of TCF in temperature dependent manner.

TABLE 3

| Temperature (°C.) | 0.15 M NaCl | | | 0.3 M NaCl | | |
|---|---|---|---|---|---|---|
| | pH 6.0 | pH 6.5 | pH 7.0 | pH 6.0 | pH 6.5 | pH 7.0 |
| 5 | 2.8 | 1.7 | 1.2 | 50.6 | 39.2 | 37.0 |
| 20 | 12.4 | 6.6 | 4.9 | 53.7 | 51.4 | 49.4 |
| 40 | 32.9 | 31.1 | 30.0 | 60.7 | 59.7 | 58.7 |

*Solubility is expressed as mg/ml.

(5) Effect of Solubilizer on Solubility of TCF

In consideration of physiological conditions to use TCF for pharmaceuticals, solutions of neutral pH of 6.6–7.2 for dissolving TCF were prepared using various amino acids as solubizers and sodium chloride to adjust osmotic pressure to about 300 mOsm. The solubility of TCF was determined at 5° C. according to the method shown in experiment (1) and the results are shown in Table 4.

TABLE 4

| Amino acid | Concentration | 0 M NaCl | 0.075 M NaCl | 0.15 M NaCl |
|---|---|---|---|---|
| — | — | — | — | 1.2 |
| Gly | 2% | 1.0 | — | — |
| | 1% | — | 3.0 | — |
| L-Ala | 2.5% | 1.5 | — | — |
| | 1.25% | — | 3.2 | — |
| L-Ser | 3% | 1.0 | — | — |
| | 1.5% | — | 1.9 | — |
| L-Met | 4% | 1.2 | — | — |
| | 2% | — | 2.0 | — |
| L Pro | 3% | 1.4 | — | — |
| | 1.5% | — | 3.0 | — |
| L-Asp.Na.H₂O | 3% | 5.3 | — | — |
| | 1.5% | — | 3.4 | — |
| L-Glu.Na.H₂O | 3% | 4.7 | — | — |
| | 1.5% | — | 3.3 | — |
| L-Arg.HCl | 3.5% | 16.4 | — | — |
| | 1.75% | — | 7.6 | — |
| D-Arg.HCl | 3.5% | 21.7 | — | — |
| | 1.75% | — | 10.3 | — |
| DL-Arg.HCl | 3.5% | 21.7 | — | — |
| | 1.75% | — | 8.5 | — |
| L-Lys.HCl | 3% | 10.4 | — | — |
| | 1.5% | — | 6.9 | — |
| L-His | 4% | 3.5 | — | — |
| | 2% | — | 3.2 | — |

*Solubility is expressed as mg/ml.

Neutral amino acids such as glycine at concentration of 1–4% gave slight increase of solubility and acidic amino acids such as sodium L-asparlate monohydrate at concentration of 1–5% increased the solubility about 3–4 times than that in the solution with no amino acid. But significant solubilizing effect of these amino acids were not found.

On the contrary, basic ammino acids such as L-arginine at concentration of 1.75–3.5% significantly increased solubility of TCF.

The solubilities were 5–15 times higher than that of no addition of amino acid. Furthermore, L-, D- and DL-forms of arginine gave same results. L-lysine at concentration of 1.5–3% also gave increase of solubility. However, L-histidine at concentration of 2–4% showed only about 3 times higher solubilities than that of no addition of amino acid.

The present invention can provide TCF pharmaceuticals of 10 mg/ml or more concentrations using basic amino acids, sodium chloride and so forth as a solubilizing agent. On the contrary, TCF dissolves at a concentration of about 1 mg/ml in neutral and isotonic solution without the solubilizing agent.

EXPERIMENT 2

Basic amino acids used in the present invention are effective to improve the stability of TCF during storage. The effect is explained by the following test experiments which show the effects of various additives on the stability of TCF during storage.

Human serum albumin (HSA) and D-mannitol were added to the solutions containing sodium chloride and/or L-arginine hydrochloride. TCF was dissolved at concentrations of 1 mg/ml in these solutions at room temperature. The prepared TCF solutions were sterilized with a filter having pore size of 0.22 μm and divided in polypropylene tubes. The tubes were kept at 5° C. or 20° C. for 1, 4 and 7 days. The tubes were ultracentrifuged by the method described in Experiment (1). The concentration of TCF in the supernatant was measured by the method of Lowry Folin and enzyme-linked immunosorbent assay (ELISA) disclosed in Japanese Un-examined Patent Publication No. 97 (1993), and residual TCF was calculated. The effects of the additives on the solubility of TCF were evaluated.

Figure 2:
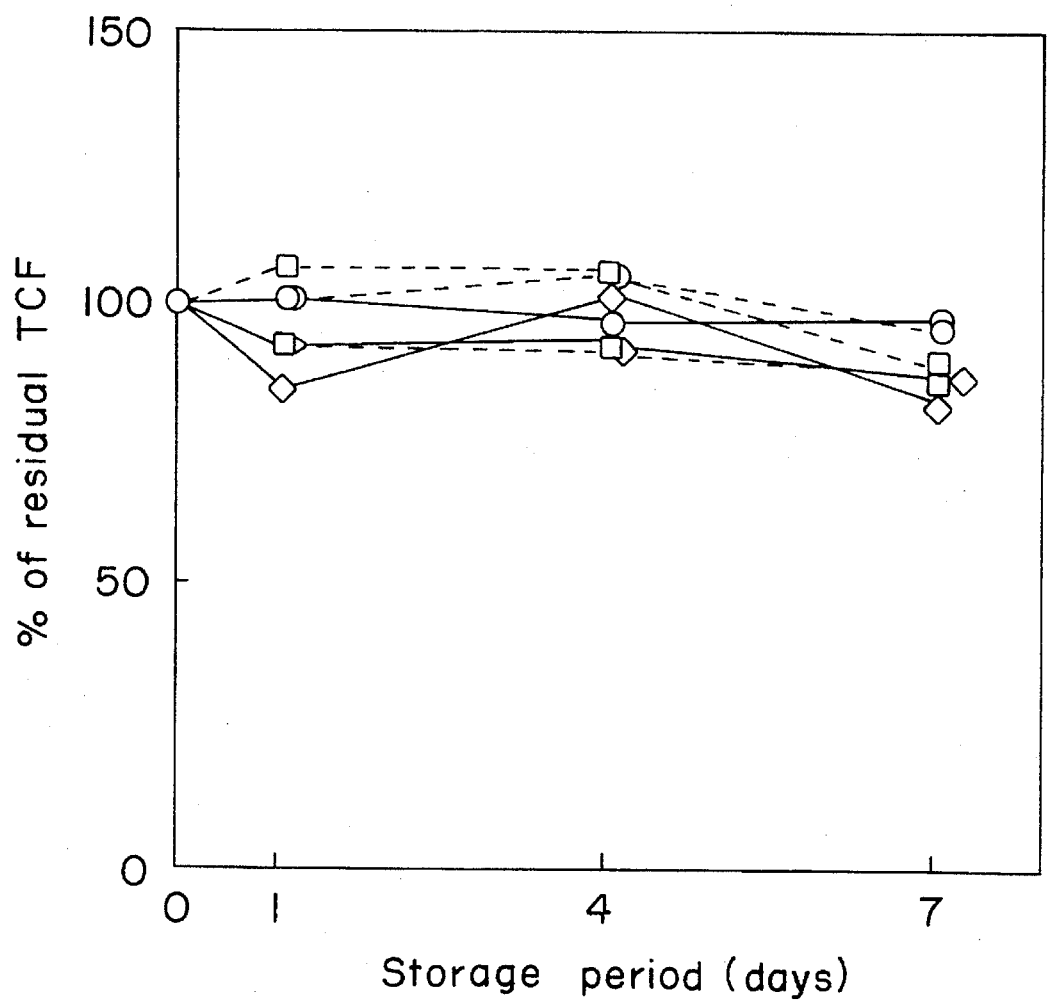
FIG. 2 shows a stability on storage of the TCF solution prepared by adding L-arginine hydrochloride and sodium chloride as dissolution adjuvants and D-mannitol as a stabilizer.
Figure 3:
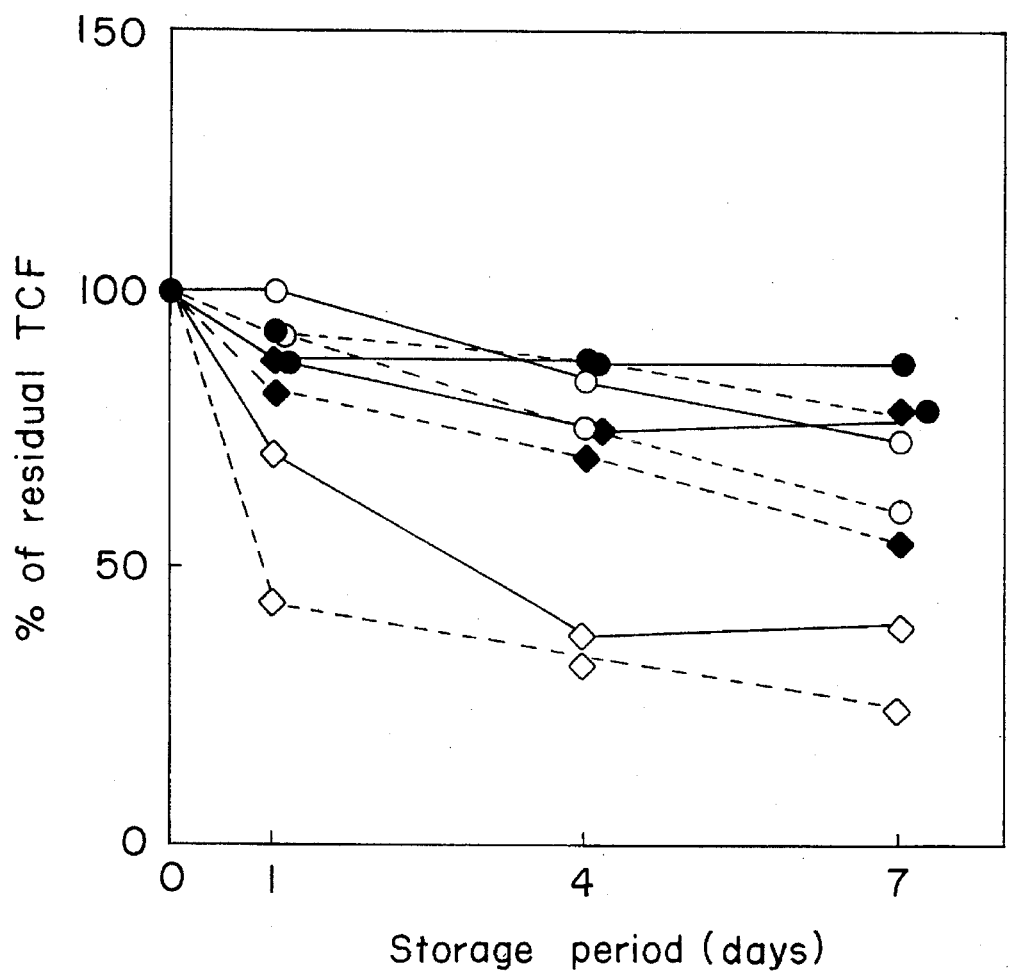
FIG. 3 shows a stability on storage of the TCF solution prepared by adding sodium chloride as an dissolution adjuvant, and human serum albumin (HSA) and D-mannitol as stabilizers.

The results are shown in FIGS. 1, 2 and 3. The values are expressed as percentage to the initial amount of TCF. As shown in the figures, L-arginine hydrochloride increased the stability of the pharmaceuticals of the present invention.

What is claimed is:

1. A tumor cytotoxic factor (TCF) composition comprising:

TCF;

a basic amino acid or a salt of a basic amino acid; and a pharmacologically acceptable organic or inorganic salt; wherein the amount of TCF is sufficient such that when the composition is dissolved or dispersed in a liquid carrier, the concentration of TCF is at least about 5 mg/ml.

2. An isotonic injectable TCF preparation having an approximately neutral pH comprising a physiologically acceptable carrier liquid containing:

at least 5 mg/ml of TCF;

a basic amino acid or salt of a basic amino acid; and a pharmacologically acceptable organic or inorganic salt.

3. The composition of claim 2 wherein the concentration of TCF is at least 10 mg/ml.

4. The composition of claim 1 or 2 wherein the basic amino acid or salt is lysine or arginine, or a salt of lysine or arginine.

5. The composition of claim 1 or 2 wherein the basic amino acid or salt thereof is present in an amount sufficient to enhance solubility in the liquid carrier of TCF at approximately neutral pH.

6. The composition of claim 1 or 2 wherein the pharmacologically acceptable salt is selected from the group consisting of sodium citrate, sodium lactate, sodium chloride, disodium hydrogen-phosphate and sodium hydrogen-carbonate.

7. The composition of claim 6 wherein the salt is sodium chloride.

8. The composition of claim 1 or 2 wherein the liquid carrier comprises water, saline or phosphate buffer.

9. The composition of claim 1 or 2 wherein said composition is in lyophilized or dried form, and is mixed with the liquid carrier prior to use.

10. A method for improving solubility of TCF in an aqueous liquid, the method comprising combining TCF with a basic amino acid or salt thereof thereby forming a homogeneous mixture; and dissolving or dispersing said mixture in the aqueous liquid.

11. The method of claim 10 wherein the concentration of TCF is at least 5 mg/ml.

12. The method of claim 10 wherein the basic amino acid or salt is lysine or arginine, or a salt of lysine or arginine.

13. The method of claim 10 wherein the basic amino acid or salt thereof is present in an amount sufficient to enhance solubility in the liquid carrier of TCF at approximately neutral pH.

14. The method of claim 10 wherein the pharmacologically acceptable salt is selected from the group consisting of sodium citrate, sodium lactate, sodium chloride, disodium hydrogen-phosphate and sodium hydrogen-carbonate.

15. The method of claim 14 wherein the salt is sodium chloride.

16. The method of claim 10 wherein the liquid carrier comprises water, saline or phosphate buffer.

17. The method of claim 10 wherein said composition is in lyophilized or dried form, and is mixed with the liquid carrier prior to use.

* * * * *